United States Patent [19]
Kochi et al.

[11] Patent Number: 5,271,923
[45] Date of Patent: Dec. 21, 1993

[54] SOLID RADIOGRAPHIC CONTRAST MEDIUM

[75] Inventors: Hiromi Kochi; Junro Amano, both of Fukuyama; Takashi Nishiyama, Kasaoka; Shin-ichi Tashiro, Kyoto, all of Japan

[73] Assignee: Manac Incorporated, Hiroshima, Japan

[21] Appl. No.: 827,605

[22] Filed: Jan. 29, 1992

Related U.S. Application Data

[62] Division of Ser. No. 459,788, Mar. 1, 1990, abandoned.

[30] Foreign Application Priority Data

Jul. 5, 1988 [JP] Japan .................. 63-165880

[51] Int. Cl.$^5$ ............................. A61K 49/04
[52] U.S. Cl. ....................... 424/5; 525/327.9; 525/333.4; 525/356
[58] Field of Search ............................ 424/5

[56] References Cited

U.S. PATENT DOCUMENTS

| | | | |
|---|---|---|---|
| 2,439,374 | 4/1948 | Leader et al. | |
| 2,832,722 | 4/1958 | Singher | 424/5 |
| 3,733,397 | 5/1973 | Bjork et al. | |
| 3,852,341 | 12/1974 | Bjork et al. | 424/5 |
| 4,406,878 | 9/1983 | DeBoer | 424/5 |
| 4,857,576 | 8/1989 | Kochi et al. | |

FOREIGN PATENT DOCUMENTS

| | | |
|---|---|---|
| 0203833 | 3/1986 | European Pat. Off. |
| WO9000408 | 1/1990 | PCT Int'l Appl. |
| 411098 | 6/1974 | U.S.S.R. |
| 606400 | 8/1948 | United Kingdom |
| 1400985 | 7/1975 | United Kingdom |

*Primary Examiner*—Bernard Lipman
*Attorney, Agent, or Firm*—Birch, Stewart, Kolasch & Birch

[57] ABSTRACT

A safe and effective solid radiographic contrast medium which comprises an iodine-substituted aromatic polymer with an iodine content of 1 to 75% by weight and which is free of side effects on the digestive system such as constipation as found in barium preparations and which has no risk of causing iodine shocks as found in aqueous iodine preparations containing meglumine sodium amidotrizoate.

6 Claims, 1 Drawing Sheet

SOLID RADIOGRAPHIC CONTRAST MEDIUM

This application is a continuation of copending application Ser. No. 07/459,788, filed on Mar. 1, 1990, now abandoned. The entire contents of which are hereby incorporated by reference.

FIELD OF THE INVENTION

The present invention relates to a solid radiographic contrast medium, more specifically to a solid iodic radiographic contrast medium which has an excellent radiographic contrast effect and which is safe with no severe side effects.

BACKGROUND OF THE INVENTION

Digestive tract radiography is essential to medical examinations for the treatment and prevention of various digestive diseases. Particularly, cancer of the digestive tract is detected at high ratios by radiography; therefore, not only patients with suspected cancer but also healthy persons, for the purpose of secondary prophylaxis, often undergo cancer examination by radiography.

The representative radiographic contrast media for digestive tract radiography are barium preparations containing barium sulfate as the active ingredient. Barium preparations possess an excellent contrast effect and chemical stability and, in addition, they are cheap. However, they are often accompanied by a problem of side effects on digestive organs such as constipation. Also, barium preparations are not applicable to those patients with perforation or acute bleeding in the digestive tract or those suspected of such a lesion. These side effects and use limitations are associated with the astringent action of barium sulfate and its nature in which it becomes clayish and solidifies like gypsum in the absence of sufficient water due to its poor fluidity and adhering and condensing properties. In fact, purgatives and other medicines are used in combination with these preparations to cope with the side effects, but this measure is not satisfactory. To solve the above-mentioned problem posed by the barium preparations, an aqueous iodic preparation has been proposed. This preparation, containing meglumine sodium amidotrizoate as the active ingredient, has no digestive tract side effects as found in barium preparations and is thus applicable to patients in whom the use of barium preparations is contraindicated. However, this preparation involves a risk of iodine shock as the most critical side effect. Iodine shock is not a frequently-occurring side effect, but it may cause serious symptoms, which may lead to death. For this reason, the use of this preparation is contraindicated for patients with a past history of iodine hypersensitivity, and much care should be given when applying it to patients with allergic constitution. In addition, the aqueous iodic preparation is relatively expensive.

Accordingly, none of the currently used radiographic contrast media are perfect. With this background, it was desired that a radiographic contrast medium which has an excellent radiographic contrast effect without severe side effects should be developed.

DETAILED DESCRIPTION OF THE INVENTION

The present inventors made investigations with the aim of developing a safe and useful radiographic contrast medium, and found that a substance obtained by substituting an aromatic polymer with iodine possesses properties favorable for digestive tract radiographic contrast media while having no side effects on the digestive tract nor eliciting a hypersensitive reaction such as iodine shock. The present inventors made further investigations based on this finding, and developed the present invention.

Accordingly, the present invention provides a solid radiographic contrast medium comprising an iodine-substituted aromatic polymer with an iodine content of 1 to 75% by weight.

The radiographic contrast medium of the present invention is a water-insoluble polymer comprising an aromatic polymer substituted with an appropriate amount of iodine. In the present specification, iodine content is expressed in values obtained by measurement in accordance with the oxygen flask combustion method specified in JIS K-6388.

It is appropriate that the iodine content of the preparation of the present invention be in the range from 1 to 75% by weight. When the iodine content of the preparation exceeds 75% by weight, the iodizing agent (e.g. iodine chloride) may be decomposed during the reaction, or a side reaction may take place which can lower the chemical stability of the iodine-substituted aromatic polymer product, since high temperature, long time reaction becomes needed for its production. For this reason, it is appropriate that the upper limit of the iodine content of the iodine-substituted aromatic polymer be about 75% by weight. Also, it is appropriate that the lower limit of the iodine content be 1% by weight, preferably 5% by weight, more preferably 20% by weight, and ideally 30% by weight, since no satisfactory contrast effect is obtained when the iodine content is below 1% by weight.

The production method for the iodine-substituted aromatic polymer is not subject to particular limitation; any method known to those skilled in the art can be used, but preference is given to the method in which an aromatic polymer is iodized with an iodizing agent. Other usable methods include the method in which an iodine-substituted aromatic compound monomer is polymerized and the method in which an iodine-substituted aromatic polymer, as an intermediate, is further subjected to cross-link polymerization.

In the present specification, the aromatic polymer means a polymer having an aromatic ring, including aromatic linear polymers and aromatic cross-linked polymers. Such polymers are known to those skilled in the art or can easily be produced by methods described in literature. For example, the aromatic cross-linked polymers described in Japanese Patent Examined Publication No. 31146/1986, West German Patent No. P3434236.2 and U.S. FWC Application No. 06/843,914 (all are involved in a joint application by MANAC Inc. and Mitsubishi Chemical Industries Ltd.) and aromatic linear polymers which contain no bifunctional or more highly functional monomers which serve as cross-linking agents in the production of these aromatic cross-linked polymers and which comprise monovinyl monomers such as aromatic monovinyl monomers are suitable for the preparation of the present invention.

Examples of aromatic linear polymers usable for the present invention include those obtained from aromatic monovinyl monomers such as styrene, vinyltoluene and vinylnaphthalene.

Examples of aromatic cross-linked polymers include those obtained by polymerization by a known method of an aromatic monovinyl monomer as described above and, as a cross-linking agent, a bifunctional or more highly functional monomer such as divinylbenzene, trivinylbenzene, divinyltoluene, divinyl diphenyl ether, ethylene glycol dimethacrylate, trimethylolpropane trimethacrylate, divinylpyridine and trivinylpyridine, and if desired, one or more other monomers which are copolymerizable with these monomers, such as acrylonitrile, methyl methacrylate, octadiene and isoprene. Also useful are those obtained by forming cross linkages between the molecular chains of aromatic linear polymers such as linear polystyrene by a known method such as the Friedel-Crafts reaction. It is preferable that the cross-linking agent (e.g., bifunctional or more highly functional vinyl monomer single substance) content of the preparation of the present invention be 1 to 50% by weight, more preferably 5 to 20% by weight.

The object of the present invention can be accomplished by use of any of the above-mentioned aromatic linear polymers and aromatic cross-linked polymers, but the latter is considered safer because it is not absorbed in living bodies due to its water insolubility associated with its three-dimensional structure. When the degree of cross-linking exceeds 5, the safety based on the insolubility is enhanced, and so this condition is preferred.

As stated above, an aromatic cross-linked polymer with a degree of cross-linking of 5 or more obtained from a combination of styrene and divinylbenzene is most suitable for accomplishing the object of the present invention. Specifically, it is preferable to use a cross-linked polymer obtained by use of polyvinyl alcohol, styrene and divinylbenzene in a ratio of about 80-99-:1-20, more preferably a polymer with a degree of cross-linking of 5 to 20 incorporating these substances in a ratio of 80-95:5-20.

Note that a porosifying agent such as toluene or dodecane may be added in cross-link polymerization. Otherwise, a ready-made polymer such as commercially available polystyrene (e.g., Dick elastin with an average molecular weight of 40,000 as determined by the GPC method) may be used.

The method of iodizing the aromatic polymer is not subject to particular limitation. For example, it is possible to use methods known to those skilled in the art such as the method in which the aromatic polymer is reacted with iodine chloride in an appropriate reaction solvent and the method in which iodine is reacted in the presence of an oxidizing agent such as iodine pentaoxide.

Examples of reaction solvents usable for iodization include carbon tetrachloride, dichloroethane and trichloroethane in cases where iodine chloride is reacted, and nitrobenzene in cases where iodine is reacted in the presence of iodine pentaoxide.

Reaction temperature is above 0° C., preferably above 60° C. It is also preferable that the reaction temperature be below the reflux temperature of the solvent used. Excessively low temperatures are undesirable because reaction rate decreases.

After completion of the reaction, the iodizing agent, catalyst and other substances which remain in the reaction system are treated and decomposed with water or an aqueous solution of alkali such as NaOH, KOH, $Na_2CO_3$ or $NaOCH_3$. Then, the reaction product is isolated by filtration, such as gravitational filtration, forced filtration by filter press, reduced pressure filtration and washing by a column chromatography, which is followed by drying. The solid product is then, if desired, pulverized to granules with an appropriate granule size to yield the solid radiographic contrast medium of the present invention.

The iodine-substituted aromatic polymer of the present invention can also be obtained not only by iodizing an aromatic polymer as described above but also by polymerizing an iodine-substituted aromatic vinyl monomer alone or by copolymerizing it with the above-mentioned vinyl monomer or, if desired, also with one or more other monomers which are copolymerizable therewith. Typical iodine-substituted aromatic vinyl monomers include iodostyrene and iodovinylnaphthalene. However, this method using an iodine-substituted aromatic vinyl monomer is subject to limitations due to polymerization during production of the monomer and other aspects; therefore, the former method, in which an aromatic polymer is iodized, is preferable.

Also, the iodine-substituted aromatic cross-linked polymer having cross linkage can also be obtained by the method in which cross linkage is formed between the molecular chains of the iodine-substituted linear polymer by a known method such as the Friedel-Crafts reaction or the method in which an iodine-substituted aromatic vinyl monomer such as iodostyrene or iodovinylnaphthalene is polymerized alone or with another monomer in the presence of a bifunctinal or more highly functional vinyl monomer such as divinylbenzene, which serves as a cross-linking agent. However, the method using an iodine-substituted linear polymer or iodine-substituted aromatic monomer is subject to limitations such as undesirable polymerization during production of the iodine-substituted monomer and difficultires in the adjustment of the degree of cross-linking of the cross-linked polymer product. Therefore, the method in which an aromatic cross-linked polymer is iodized as described above is most preferable.

The iodine-substituted aromatic polymers mentioned above are all useful as radiographic contrast media, but preference is given to iodine-substituted aromatic cross-linked polymers since they are not absorbed in vivo due to water insolubility, and since they are relatively safe. More preferable embodiments are iodine-substituted aromatic cross-linked polymers with a degree of cross-linking between 5 and 20.

Specifically, iodine substituted cross-linked polymers comprising styrene and divinylbenzene are preferable. Also suitable for use is iodized commercially available polystyrene.

The solid radiographic contrast medium of the present invention, insoluble in water, is pulverized into granules with an appropriate granule size and used in the form of an aqueous suspension. Granule size should be adjusted as appropriate for the purpose of use. For example, when using for the radiography of digestive organs, the solid radiographic contrast medium of the present invention are prepared as fine granules with an average granule size of between 0.01 and 20 microns, preferably between 0.1 and 10 microns. When the average granule sizes exceed these values, the resolution of radiograms lowers and the detection of lesions is hampered.

The adjustment of granule size can be conducted using known methods of pulverization such as dry or wet pulverization using pulverizers such as ball mills, vibration mills and pin mills.

The solid radiographic contrast medium of the present invention can be formulated with foaming agents such as sodium hydrogen carbonate, tartaric acid and glutamic acid hydrochloride; aromatic sweeteners; surfactants such as sorbitol; and other excipients as necessary. When using the solid radiographic contrast medium of the present invention in the form of such a composition, it is preferable for convenient use that the iodine content of the solid radiographic contrast medium be 20 to 70% by weight.

The use of the solid radiographic contrast medium of the present invention is not limited to the digestive tract but is also applicable to radiography of other sites. For example, the contrast medium of the present invention is considered particularly useful in dental treatment because it possesses high affinity to resins. Examples of such usage include the use in which it is mixed in a filling agent to monitor the occurrence and progress of dental caries after treatment and the use in which it is mixed in an impression agent for obtaining local impression before artificial dental root implantation to check the residence of the impression agent and to totally remove it.

The acute toxicity of the solid radiographic contrast medium of the present invention was determined to be more than 5,000 mg/kg $LD_{50}$ in oral administration in experiments with mice, rats and rabbits. Also, as shown in the experiments given later, neither post-therapeutic constipation nor iodine shock due to repeated administration was observed in mice or rats. These results suggest that the preparation of the present invention is very safe.

The stability of the solid radiographic contrast medium of the present invention in acid, alkali and organic solvents was determined in elution tests using a 5% aqueous solution of hydrochloric acid, a 5% aqueous solution of sodium hydroxide and 95% ethanol; component elution was not noted at all.

Furthermore, when water was evaporated off from suspensions of the solid radiographic contrast medium of the present invention, there was no tendency to exhibit an adhesive property or become clayish.

The radiographic contrast performance of the preparation of the present invention was assessed by the method in which X ray is irradiated to test pieces formed from the preparation and the contrast state is examined; the contrast effect was found to be in proportion to the preparation content in the test pieces, i.e., a contrast performance was confirmed (see FIGS. 1 and 2).

BRIEF DESCRIPTION OF THE DRAWINGS

FIG. 1 shows the state of arrangement of these three test pieces, i.e., 1), 2) and 3), which are placed to take radiography.

Figure 1:
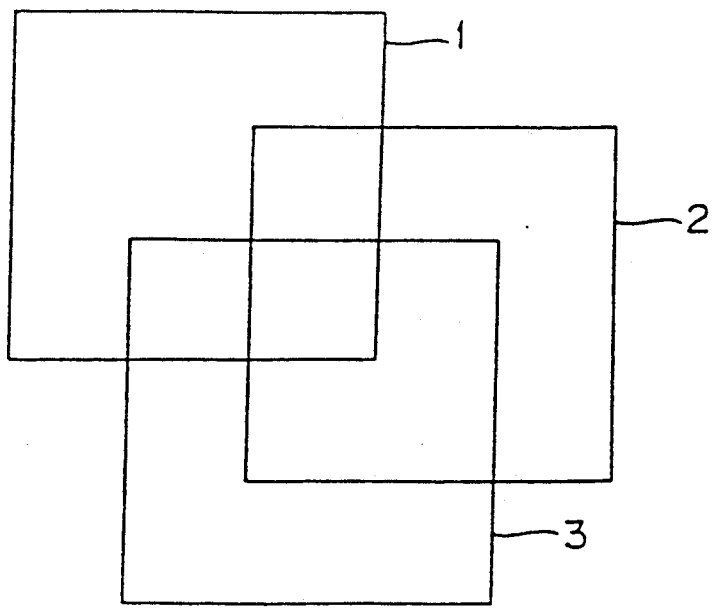
FIG. 1: The solid radiographic contrast medium prepared in Example 1 was pulverized to granules with a granule size of about 5μ and dispersed in a solution of polymethyl methacrylate in toluene (40/50, w/w). After removal of solvent, the dispersion was formed into a plate of 20×30 cm with a thickness of about 1.5 mm. From this plate, 4 cm-square test pieces were cut.

The denser the color is, the higher the contrast effect is.

PREFFERED EMBODIMENT OF THE INVENTION

The present invention is hereinafter described in more detail by means of the following examples, but the invention is not by any means limited by these examples.

Note that the figures for the iodine content of the iodine-substituted aromatic polymers given in the present specification are those obtained by measurement in accordance with the oxygen flask combustion method specified in JIS K-6388 as follows:

ANALYSIS OF IODINE CONTENT

A 0.01g sample was wrapped in ashless filter paper and combusted in a combustion flask saturated with oxygen in the presence of 0.01% aqueous hydrogen peroxide as the absorbing liquid. Then, the absorbing liquid was neutralized with a 0.1N aqueous solution of KOH and filled up to reach 100 ml in a measuring cylinder to yield a sample solution. This solution, in an amount of 100 μl, was injected into an ion chromatography column (CCPD system, produced by Toso). The peak area was calculated and the iodine ion concentration of the sample solution was determined on the basis of the calibration curve drawn previously.

EXAMPLE 1

Iodine-substituted Aromatic Cross-linked Polymer
(1) Preparation of aromatic cross-linked polymer 500 ml of water and 1 g of polyvinyl alcohol were placed in a reactor and heated to 80° to 90° C. while stirring. To this mixture was added a separately prepared mixed solution of 10 g of styrene, 1 g of divinylbenzene, 5 g of toluene, 5 g of dodecane and 0.2 g of benzoyl peroxide, and this was followed by vigorous stirring at 80° to 90° C. After 24 hours of polymerization reaction, the reaction mixture was filtered, washed with hot water and dried to yield 10 g of a cross-linked polymer.

(2) Iodization 25 g of the cross-linked polymer prepared in (1) above was suspended in 100 ml of dichloroethane. To this suspension was added 75 g of iodine monochloride over a period of 60 minutes while stirring at room temperature. After completion of the addition, reaction was carried out for 2 more hours with refluxing. The reaction mixture was neutralized by sequential addition of 40 ml of water and 60 g of a 48% aqueous solution of NaOH. The mixture was filtered to separate the resulting iodine-substituted aromatic cross-linked polymer, which was then washed with dichloroethane, dried and then pulverized to yield 49 g of a solid radiographic contrast medium with an iodine content of 52% by weight.

EXAMPLE 2

Iodine-substituted Aromatic Cross-linked Polymer 10 g of cross-linked polymer was obtained in exactly the same manner as in Example 1 except that neither the porosifying agent toluene nor dodecane was added.

Then, except that 25 g of this cross-linked polymer was used, exactly the same procedure as in Example 1 (2) was followed to yield 55 g of a solid radiographic contrast medium with an iodine content of 62% by weight.

EXAMPLE 3

Iodine-substituted Aromatic Cross-linked Polymer 25 g of a cross-linked polymer prepared in the same manner as in Example 1 (1) was suspended in 100 ml of nitrobenzene. To this suspension was added a separately prepared solution comprising 20 g of iodine, 10 g of iodine pentaoxide, 30ml of carbon tetrachloride and 60 ml of 50% sulfuric acid over a period of 60 minutes while stirring at 90° C. After reaction at 90° C. for 10 more hours, 100ml of water was added and the water layer and the organic layer were separated from each other. The organic layer was washed with a 30% aqueous solution of NaOH. After 50 ml of nitrobenzene was distilled off under reduced pressure, the residual solution was poured into 1000 ml of methanol. Then, the product was collected by filtration, dried and pulverized to yield 41 g of a solid radiographic contrast medium with an iodine content of 42% by weight.

EXAMPLE 4

Iodine-substituted Aromatic Cross-linked Polymer

Except that 25 g of a cross-linked polymer prepared in the same manner as in Example 2 was used, exactly the same procedure as in Example 3 was followed to yield 43 g of a solid radiographic contrast medium with an iodine content of 45% by weight.

EXAMPLE 5

Iodine-substituted Aromatic Cross-linked Polymer 500 ml of water and 1 g of polyvinyl alcohol were placed in a reactor and heated to 80° to 90° C. while stirring. To this mixture was added a separately prepared mixture of 20 g of p-iodostyrene, 2 g of divinylbenzene and 0.2 g of benzoyl peroxide. This was followed by vigorous stirring at 80° to 90° C. and 24 hours of polymerization reaction. Then, the resulting solid was filtered, washed with hot water and then washed with dichloroethane, dried and pulverized to yield 10 g of a solid radiographic contrast medium with an iodine content of 55% by weight.

EXAMPLE 6

Iodine-substituted Aromatic Linear Polymer

To a mixed solution of 25 g of a commercially available low molecular polystyrene (Dick elastin, average molecular weight of 40,000 as determined by the GPC method) and 100 ml of dichloroethane, was added 75 g of iodine monochloride over a period of 60 minutes while stirring the mixed solution at room temperature. After completion of the addition, reaction was carried out for 2 hours with refluxing. Then, the reaction mixture was neutralized by sequential addition of 40 ml of water and 60 g of a 48% aqueous solution of NaOH. After 60 ml of the solvent dichloroethane was distilled off under reduced pressure, the resulting solid iodine-substituted aromatic polymer was collected by filtration, washed with a mixed solvent of water and methanol (water: methanol = 1:1), dried and pulverized to yield 65 g of a solid radiographic contrast medium with an iodine content of 68% by weight.

EXAMPLE 7

Iodine-substituted Aromatic Linear Polymer

To a mixed solution comprising 25 g of the same low molecular polystyrene as in Example 6 and 100 ml of nitrobenzene, was added a separately prepared solution comprising 20 g of iodine, 10 g of iodine pentaoxide, 30 ml of carbon tetrachloride and 60 ml of 50% sulfuric acid over a period of 60 minutes while stirring the mixed solution at 90° C. Then, after reaction at 90° C. for 10 hours, 100 ml of water was added and the water layer and the organic layer were separated from each other. The organic layer was washed with a 30% aqueous solution of NaOH. After 50 ml of the nitrobenzene was distilled off under reduced pressure, the residual solution was poured into 1000 ml of methanol. The resulting solid was collected by filtration, dried and pulverized to yield 62 g of a solid radiographic contrast medium with an iodine content of 64% by weight.

The solid radiographic contrast media obtained in the above examples were assessed by the methods described in the following tests; these solid radiographic contrast media were found to possess very excellent properties.

TEST 1

Radiographic Contrast Effect Validation Test

The solid radiographic contrast medium prepared in Example 1 was assessed as to contrast performance by the two methods described below.

METHOD 1

The solid radiographic contrast medium prepared in Example 1 and the uniodized cross-linked polymer prepared in Example 1 (1) (for blank data) were each pulverized to granules with an average granule size of 5 microns. Then, 10 parts by weight of each of these powders was uniformly dispersed in 100 parts by weight of a toluene solution of polymethyl methacrylate (polymethyl methacrylate/toluene = 40/50 by weight). The resultant dispersion was placed in a quadrangular vat of 20 cm × 30 cm. The vat containing the dispersion was placed in a reduced pressure drier (temperature 50° C., atmospheric pressure 100 mmHg) and the toluene was distilled off to yield a rectangular form of about 1.5 mm in thickness. From each form, 6 test pieces in a 4 cm square tile form were prepared.

Figure 2:
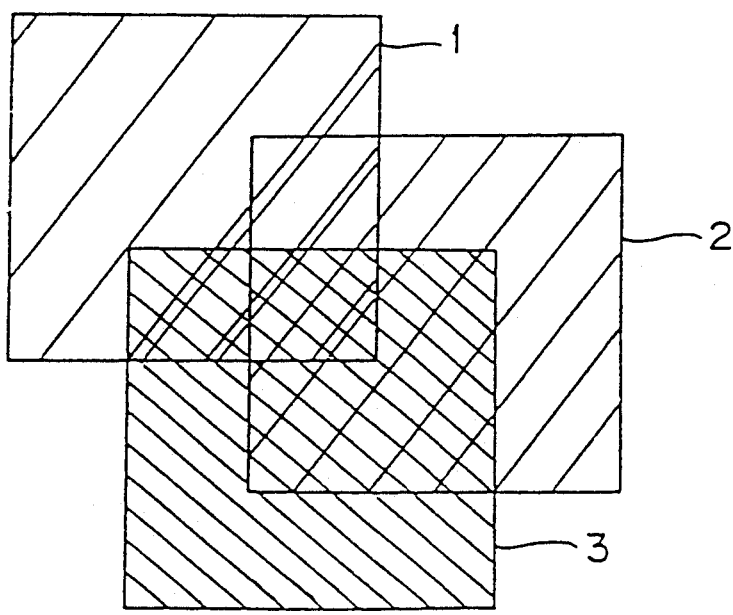
FIG. 2: The radiogram obtained using test pieces arranged in the state of FIG. 1, wherein A) shows the result obtained using a single test piece, B) shows the result obtained using two test pieces superposed together and C) shows the result obtained using three test pieces superposed together. The density of color increased in the order of A, B and C.

These test pieces were arranged as shown in FIG. 1, and radiograms were taken at an intensity of 10 MAS. The results are shown in FIG. 2. FIG. 1 shows the arrangement of these test pieces, i.e., 1), 2) and 3), before taking radiograms. FIG. 2 is the radiogram obtained by X ray irradiation of the test pieces 1), 2) and 3) arranged as illustrated in FIG. 1, wherein A shows the result obtained using a single test piece, B shows the result obtained using two test pieces superposed together, and C shows the result obtained using three test pieces superposed together. The density of color increased in the order of A, B and C. The denser the shaded portion is, the higher the contrast effect is.

As is evident from these figures, the radiographic performance of the test pieces prepared from the solid radiographic contrast medium of the present invention is in proportion to their thickness. This suggests that the preparation of the present invention possesses excellent radiographic performance. On the other hand, the blank cross-linked polymer exhibited no radiographic contrast effect.

METHOD 2

Samples were prepared by mixing the solid radiographic contrast medium prepared in Example 1 and the uniodized cross-linked polymer prepared in Example 1

(1) in ratios of 0:100, 2:98, 10:90, 40:60, 60:40 and 80:20. Then, each sample was packed in a polyethylene tube of 5 mm in diameter and 5 cm in length. After sealing both ends of the tube, each sample was subjected to radiography at an intensity of 4 MAS. No contrast effect was obtained in the sample with a mixing ratio of 0:100. The sample with a mixing ratio of 2:98 (iodine content was about 1% by weight) showed a slight effect. The sample with a mixing ratio of 10:90 showed a clear effect. In other words, it was found that the radiographic definition increases as the mixing ratio of the solid radiographic contrast medium increases.

TEST 2

Eluted Component Detection Test

The stability of the solid radiographic contrast medium prepared in Example 1 in acid, alkali and organic solvent was determined in a qualitative extraction test using these solvents.

The acid used was a 5% aqueous solution of hydrochloric acid; the alkali used was a 5% aqueous solution of sodium hydroxide; the organic solvent used was 95% ethanol. Elution was conducted using 10 g of extraction solvent per 2 g of the solid contrast medium. The extract was analyzed for eluates using a spectrophotometer on the basis of the absorbance in the ultraviolet through visual light range at 550 to 190 nm. No eluates were detected from the solid radiographic contrast medium.

TEST 3

Confirmation Test for Adhesive and Other Properties

A suspension of the solid radiographic contrast medium prepared in Example 1 was compared with a barium sulfate dispersion as to adhesive and other properties by the method described below. Also compared were properties after water evaporation.

10 parts by weight of each of the solid radiographic contrast medium and barium sulfate was taken in a 200 ml beaker. To each beaker was added 20 parts by weight of water to disperse the content to yield a suspension, and the adhesive property was compared. Then, each beaker containing each suspension was heated over an electric heater to gradually evaporate the water, during which changes in properties were observed. The solid radiographic contrast medium did not exhibit an adhesion property like barium sulfate. Also, when water was evaporated, the solid radiographic contrast medium did not become clayish as does barium sulfate.

These tests all concern the solid radiographic contrast medium prepared in Example 1, but similar results were obtained from the solid radiographic contrast media prepared in Examples 2 through 7.

Next, the effect and contrast performance of the solid radiographic contrast medium of the present invention in vivo were examined.

The acute toxicity of the solid radiographic contrast medium of the present invention was assessed by the acute toxicity test method described in "Toxicity Test Guideline for Pharmaceuticals" (Pharmaceutical Affairs Bureau, Ministry of Health and Welfare, Japan) using mice, rats and rabbits. The test revealed that the $LD_{50}$ of the solid radiographic contrast medium of the present invention exceeds 5,000 mg/kg on oral administration.

Next, the radiographic effect and various side effects were assessed by the methods described in the following experiments.

EXPERIMENT 1

Effect of the Radiographic Contrast Medium in Animals

The animals used in the experiment were 5 mice and 5 rats.

A 1% solution of surfactant, polyoxyethylene cetyl ether, was prepared. This solution was gradually added to the solid radiographic contrast medium (prepared in the same manner as in Example 1) in a porcelain mortar with stirring to yield a 400 g/l sample suspension.

The resulting sample suspension was orally administered to each experimental animal via a gastric sound at a dose of about 6 g as the solid radiographic contrast medium per kg body weight. Immediately and 12 hours after administration, each animal was subjected to radiography under anesthetic conditions to assess the radiographic contrast effect. The X ray intensity at radiography was 10 mMAS for mice and 20 mMAS for rats. Also examined was the state of excretion for constipation at 12 hours following administration. A good contrast effect was obtained, and no constipation symptoms were noted. The results are shown in Table 1.

TABLE 1

Test Results in Single Administration

| | Body Weight (g) | Suspension (ml) | Solid radiographic contrast medium (g) | Contrast condition | Residues detected after 12 hours |
|---|---|---|---|---|---|
| Mouse | | | | | |
| 1 | 31 | 0.5 | 0.2 | Good | None |
| 2 | 32 | 0.5 | 0.2 | Good | None |
| 3 | 31 | 0.5 | 0.2 | Good | None |
| 4 | 31 | 0.5 | 0.2 | Good | None |
| 5 | 33 | 0.5 | 0.2 | Good | None |
| Rat | | | | | |
| 1 | 107 | 1.5 | 0.6 | Good | None |
| 2 | 110 | 1.5 | 0.6 | Good | None |
| 3 | 108 | 1.5 | 0.6 | Good | None |
| 4 | 112 | 1.5 | 0.6 | Good | None |
| 5 | 108 | 1.5 | 0.6 | Good | None |

Next, a sample suspension prepared in the same manner as above was again administered at 3 and 6 weeks following the first administration and the animals were examined for iodine shock. No iodine shock was noted. The results are shown in Table 2.

TABLE 2

The Occurance of Iodine Shock in Repeated Administration

| | 3 weeks after the initial administration | | | 6 weeks after the initial administration | | |
|---|---|---|---|---|---|---|
| | Suspension (ml) | Solid radiographic contrast medium (g) | Iodine shock | Suspension (ml) | Solid radiographic contrast medium (g) | Iodine shock |
| Mouse | | | | | | |
| 1 | 0.5 | 0.2 | None | 0.5 | 0.2 | None |
| 2 | 0.5 | 0.2 | None | 0.5 | 0.2 | None |
| 3 | 0.5 | 0.2 | None | 0.5 | 0.2 | None |
| 4 | 0.5 | 0.2 | None | 0.5 | 0.2 | None |
| 5 | 0.5 | 0.2 | None | 0.5 | 0.2 | None |
| Rat | | | | | | |
| 1 | 1.5 | 0.6 | None | 1.5 | 0.6 | None |
| 2 | 1.5 | 0.6 | None | 1.5 | 0.6 | None |
| 3 | 1.5 | 0.6 | None | 1.5 | 0.6 | None |

TABLE 2-continued

The Occurance of Iodine Shock in Repeated Administration

| | 3 weeks after the initial administration | | | 6 weeks after the initial administration | | |
|---|---|---|---|---|---|---|
| | Suspension (ml) | Solid radiographic contrast medium (g) | Iodine shock | Suspension (ml) | Solid radiographic contrast medium (g) | Iodine shock |
| 4 | 1.5 | 0.6 | None | 1.5 | 0.6 | None |
| 5 | 1.5 | 0.6 | None | 1.5 | 0.6 | None |

The solid radiographic contrast medium of the present invention can be widely used for digestive tract radiography for therapeutic and preventive purposes because it causes neither side effects on the digestive system nor iodine shock and, in addition, it possesses excellent contrast performance. On administration, the preparation can be suspended in water to prepare a suspension of an appropriate concentration and then given by oral administration, intraintestinal injection or another means. The administration dose can be 20 to 300 ml of a contrast medium suspension containing 100 to 700 g of iodine per liter in a single administration in case of oral administration. In case of intraintestinal injection, the desired effect can be obtained when it is administered at doses of 200 to 3000 ml of a contrast medium suspension prepared to a concentration of 10 to 700 g/l as iodine content in a single administration.

Also, when adding to a filling agent to monitor the progress of dental caries for dental application, the contrast medium is mixed in a ratio of 5 to 50% by weight, relative to 30 to 50% by weight of a dental base (e.g., methyl methacrylate) and 30 to 50% by weight of spherical silica. When mixing into an impression agent, the contrast medium is preferably used in a ratio of 5 to 70% by weight.

What is claimed is:

1. A method for taking a radiograph, comprising administering to a subject an iodine-substituted aromatic polymer having an iodine content of 1 to 75% by weight as a radiographic contrast medium, wherein said aromatic polymer in said iodine-substituted aromatic polymer is an aromatic linear polymer obtained from one or more aromatic monovinyl monomers selected from the group consisting of styrene, vinyltoluene and vinylnaphthalene.

2. A method for taking a radiograph, comprising administering to a subject an iodine-substituted aromatic polymer having an iodine content of 1 to 75% by weight as a radiographic contrast medium, wherein said aromatic polymer in said iodine-substituted aromatic polymer is an aromatic cross-linked polymer obtained from a combination of one or more aromatic monovinyl monomers selected from the group consisting of styrene, vinyltoluene and vinylnaphthalene and one or more cross-linking agents which are bifunctional or more highly functional vinyl monomers selected from the group consisting of divinylbenzene, trivinylbenzene, divinyltoluene, divinyldiphenyl ether, ethylene glycol dimethacrylate, trimethylolpropane trimethacrylate, divinylpyridine and trivinylpyridine.

3. A method for taking a radiograph, comprising administering to a subject an iodine-substituted aromatic polymer having an iodine content of 1 to 75% by weight as a radiographic contrast medium, wherein said aromatic polymer in said iodine-substituted aromatic polymer is an aromatic cross-linked polymer obtained from a combination of styrene as an aromatic monovinyl monomer and divinylbenzene as a cross-linking agent.

4. A method for taking a radiograph, comprising administering to a subject an iodine-substituted aromatic polymer having an iodine content of 1 to 75% by weight as a radiographic contrast medium, wherein said aromatic polymer in said iodine-substituted aromatic polymer is an aromatic cross-linked polymer obtained from a combination of one or more aromatic monovinyl monomers selected from the group consisting of styrene, vinyltoluene and vinylnaphthalene and one or more other monomers selected form the group consisting of acrylonitrile, methyl methacrylate, octadiene and isoprene.

5. A method for taking a radiograph, comprising administering to a subject an iodine-substituted aromatic polymer having an iodine content of 1 to 75% by weight as a radiographic contrast medium, wherein said aromatic polymer in said iodine-substituted aromatic polymer is an aromatic cross-linked polymer obtained from a combination of polyvinyl alcohol, styrene and divinylbenzene.

6. A method for taking a radiograph, comprising administering to a subject an iodine-substituted aromatic polymer having an iodine content of 1 to 75% by weight as a radiographic contrast medium, wherein said aromatic polymer in said iodine-substituted aromatic polymer is polystyrene.

* * * * *